US010806124B2

(12) United States Patent
Karimpour

(10) Patent No.: US 10,806,124 B2
(45) Date of Patent: Oct. 20, 2020

(54) SYSTEM AND METHOD OF DETERMINING THE HEALTH AND GENDER OF A CHICK

(71) Applicant: Applied LifeSciences and Systems, LLC, Raleigh, NC (US)

(72) Inventor: Ramin Karimpour, Raleigh, NC (US)

(73) Assignee: Applied LifeSciences and Systems, LLC, Raleigh, NC (US)

(*) Notice: Subject to any disclaimer, the term of this patent is extended or adjusted under 35 U.S.C. 154(b) by 111 days.

(21) Appl. No.: 15/775,706

(22) PCT Filed: Nov. 11, 2016

(86) PCT No.: PCT/US2016/061536
§ 371 (c)(1),
(2) Date: May 11, 2018

(87) PCT Pub. No.: WO2017/083654
PCT Pub. Date: May 18, 2017

(65) Prior Publication Data
US 2018/0353081 A1 Dec. 13, 2018

Related U.S. Application Data

(60) Provisional application No. 62/349,981, filed on Jun. 14, 2016, provisional application No. 62/254,737, filed on Nov. 13, 2015.

(51) Int. Cl.
*A01K 13/00* (2006.01)
*A01K 45/00* (2006.01)
(Continued)

(52) U.S. Cl.
CPC ............ *A01K 13/003* (2013.01); *A01K 45/00* (2013.01); *A01K 61/13* (2017.01); *A61B 5/0033* (2013.01);
(Continued)

(58) Field of Classification Search
None
See application file for complete search history.

(56) References Cited

U.S. PATENT DOCUMENTS 3,994,292 A 11/1976 Goodwin
4,417,663 A 11/1983 Suzuki
(Continued)

FOREIGN PATENT DOCUMENTS

EP 2579188 10/2013
WO 2012008843 A1 1/2012
(Continued)

OTHER PUBLICATIONS

Gershman, Y., "A Simple Way to Determine the Sex of One-Day Poultry Chickens"; The Papers of Independent Authors [online]; vol. 28, DNA 2014, [https://vixra.org/pdf/1405.0016v1.pdf].
(Continued)

*Primary Examiner* — Dov Popovici
(74) *Attorney, Agent, or Firm* — Kathleen M. Lynch; Olive Law Group, PLLC

(57) ABSTRACT

A first system for determining the relative health of a chick having a first moving platform to support a chick, a first image capture device, a first database having a library of digital images relating to healthy and unhealthy chicks and a computer processor in communication with the image capture device and database. A second system for determining the gender of a chick includes a second moving platform, a second image capture device, stimuli directed at the chick to cause the chick to open its wings. The second system also includes a second database having wing patterns of male and female chicks of the breed of the chick on the second moving platform and a second computer processor in communication with the second image capture device and the second database.

18 Claims, 7 Drawing Sheets

(51) Int. Cl.

| | | |
|---|---|---|
| *A61B 5/00* | (2006.01) | |
| *A61D 7/00* | (2006.01) | |
| *G16H 50/20* | (2018.01) | |
| *A61D 17/00* | (2006.01) | |
| *A61D 19/00* | (2006.01) | |
| *A61D 1/02* | (2006.01) | |
| *B65G 15/30* | (2006.01) | |
| *A61D 3/00* | (2006.01) | |
| *G06T 7/00* | (2017.01) | |
| *A01K 61/13* | (2017.01) | |
| *G16H 20/17* | (2018.01) | |
| *A61M 5/30* | (2006.01) | |
| *A61M 5/42* | (2006.01) | |

(52) U.S. Cl.
CPC .............. *A61B 5/0077* (2013.01); *A61B 5/43* (2013.01); *A61B 5/70* (2013.01); *A61B 5/7282* (2013.01); *A61D 1/025* (2013.01); *A61D 3/00* (2013.01); *A61D 7/00* (2013.01); *A61D 17/00* (2013.01); *A61D 19/00* (2013.01); *A61M 5/30* (2013.01); *A61M 5/427* (2013.01); *B65G 15/30* (2013.01); *G06T 7/001* (2013.01); *G16H 20/17* (2018.01); *G16H 50/20* (2018.01); *A61B 2503/40* (2013.01); *A61B 2576/00* (2013.01); *A61M 2250/00* (2013.01); *B65G 2201/02* (2013.01); *G06T 2207/30128* (2013.01); *Y02A 90/26* (2018.01)

(56) References Cited

U.S. PATENT DOCUMENTS

| | | | |
|---|---|---|---|
| 4,449,968 A | 5/1984 | Peterson | |
| 4,850,997 A | 7/1989 | Dubose | |
| 5,101,767 A | 4/1992 | Williams et al. | |
| 5,626,101 A | 5/1997 | Kuhl | |
| 6,029,080 A | 2/2000 | Reynnels et al. | |
| 6,396,938 B1 * | 5/2002 | Tao | G06K 9/2018 209/509 |
| 6,512,839 B1 | 1/2003 | Toelken | |
| 7,004,112 B2 | 2/2006 | Gorans | |
| 7,066,112 B2 | 6/2006 | Gorans | |
| 7,367,284 B2 | 5/2008 | Gorans | |
| 8,019,125 B2 | 9/2011 | Nadreau et al. | |
| 8,297,231 B2 | 10/2012 | Yanai et al. | |
| 8,397,670 B2 | 3/2013 | Van Den Berg | |
| 8,677,941 B2 | 3/2014 | Yanai et al. | |
| 9,179,651 B2 | 11/2015 | McKay | |
| 2001/0035370 A1 | 11/2001 | Yavnai et al. | |
| 2005/0098121 A1 | 5/2005 | Gorans et al. | |
| 2009/0000915 A1 | 1/2009 | Nadreau et al. | |
| 2010/0198024 A1 | 8/2010 | Elazari-Volcani et al. | |
| 2010/0310589 A1 | 12/2010 | Kumar | |
| 2013/0125835 A1 | 5/2013 | Sinn et al. | |
| 2014/0069336 A1 | 3/2014 | McKay | |
| 2014/0155756 A1 | 6/2014 | Elazari-Volcani | |
| 2015/0289478 A1 | 10/2015 | McGlone et al. | |
| 2015/0320010 A1 | 11/2015 | Schippers | |

FOREIGN PATENT DOCUMENTS

| | | |
|---|---|---|
| WO | WO/2014/118788 A2 | 8/2014 |
| WO | 2015112786 A1 | 7/2015 |

OTHER PUBLICATIONS

N.T. Guy, et al., "Development of Epileptic Activity in Embryos and Newly Hatched Chicks of the Fayomi Mutant Chicken"; Epilepsia, vol. 36, No. 1, Jan. 1995 [https://pubmed.ncbi.nlm.nih.gov/8001501/].

Office Action issued by Federal Service for Intellectual Property (Russia) against Application No. 2018117356/10(027024) on Mar. 4, 2020.

English translation of Office Action issued by Federal Service for Intellectual Property (Russia) against Application No.2018117356/10(027024) on Mar. 4, 2020.

Substantive Examination Report issued by Directorate General of Intellectual Property (Indonesia) against Application No. PID201804018 on May 27, 2020.

English summary, dated Jun. 3, 2020, of Substantive Examination Report issued by Directorate General of Intellectual Property (Indonesia) against Application No. PID201304013 on May 27, 2020.

Communication pursuant to Article 94(3) EPC from the European Patent Office against Application No. 16865084.4-1011 dated Mar. 12, 2020.

* cited by examiner

SYSTEM AND METHOD OF DETERMINING THE HEALTH AND GENDER OF A CHICK

PRIORITY

This application claims priority from U.S. provisional patent application Ser. No. 62/254,737, filed Nov. 13, 2015, and U.S. provisional patent application Ser. No. 62/349,981 filed Jun. 14, 2016. The contents of each are incorporated herein in their entirety.

FIELD

The embodiments described herein are directed to systems and methods for detecting the relative health and gender of a day old chick. With regard to unhealthy chicks, they are separated from the flock once any illness or injury is detected. With regard to gender determination, once detected, the chicks are separated by gender.

BACKGROUND

There are essentially three types of poultry that are processed in today's mass production environment: broilers, breeders and layers. The broilers are grown and slaughtered at maturity for human consumption. Breeders are raised to breed broilers or layers, and layers are raised to lay eggs for human and animal consumption. In each case, as chicks hatch, they are quickly processed and moved to the next stage of their life. Day old chicks are vulnerable to disease and infection. Due to the crowded conditions in which chicks hatch and live, any chick born with an abnormality or disease may be in a position to infect a multitude of other chicks in the surrounding area. Thus it is critical to the health of the flock to remove any chick having a disease or malformation that could cause illness to other chicks. Moreover, it is only humane to remove any seriously ill chicks or disabled chicks so that they can be humanely euthanized and disposed of before causing further injury to themselves.

Day old broiler chicks are processed quickly in hatcheries and are swiftly transported to "Growth Out Farms" where they will live and grow to desire weight for consumption. There are two common maladies that afflict some chicks. The first is a failure of the abdominal wall to close after absorption of the yolk sac. In such a case, the chick hatches with an open abdominal cavity. This condition is typically terminal. If left undetected for any length of time, the open wound will attract unwanted bacteria and infection to the area and ultimately the death of the chick.

The second affliction is a malformed or disabled leg or foot or malformed beak or eye. Chicks with malformed legs and feet are unable to withstand the rigors of a mass farming environment, get adequate feed, and water in "Growth Out Farm" and consequently never grow as well as their healthy counterparts. Thus, they need to be removed as quickly as possible.

Thus, there is a need to quickly and efficiently inspect day old chicks to determine whether or not they are sufficiently healthy to withstand the rigors of the poultry production environment. In addition, there is a need to quickly and efficiently detect any physical abnormalities in day old chicks so that those with such abnormalities may be separated from the otherwise healthy flock.

Early gender determination of a chick is also important in poultry production to ensure that the sexes are separated out as soon as possible to ensure efficient investment of appropriate resources. Layer males have no value and similarly a limited number of breeder males are necessary. In the case of the broilers, male broilers are less desirable. The Feed Conversion Ratio (FCR), or cost of feed per weight gained is the main driver for the lack of favorability of broiler males.

Determining the gender of a day old chick has been a common practice in the poultry industry since the early 1900's. Manual vent and feather sexing have been used over the years by the industry to separate male and female chicks. Both methods are considered to be unfriendly to chicks based on the manual handling of the chicks, and increase the seven-day mortality of sexed chicks.

It is known that the gender of a day old chick can be determined by the chick's wing feathers. The feather pattern and length at the bend in the wing vary between male and female day old chicks. However, the present method of manually causing the chick's wings to spread increases the chick's chances for disease and injury. Moreover, the manual methodologies are labor intensive and are likely to cause repetitive injuries to the workers over time.

Thus, there is a need to quickly and automatically inspect day old chicks to determine their sex and subsequently separate them by sex.

SUMMARY

The embodiments described herein include a system having a device for positioning a chick on a moving platform, and an image capturing device to capture at least one electronic image of the chick on the moving platform. The system further includes a database containing electronic images of healthy and unhealthy chicks within the chick's breed, and an image processor in communication with the image capture device and the database. When the captured image of the chick is sent to the image processor, it is compared to the database of chick images and if the image of the chick deviates from the images of healthy chicks in the database or matched with images of unhealthy chicks or presents any anomalies, the chick is separated from the flock.

The positioning device may be a conveyor. The image taken of the chick may be a frontal image. The image taken of the chick may be of its torso. The image taken of the chick may be of its legs, face and feet.

The embodiments herein described further include a method for determining the health of a day old chick including the steps of positioning a chick on a moving platform and capturing at least one electronic image of the chick on the moving platform. The method also includes providing a database containing electronic images of healthy chicks within the chick's breed and providing an image processor in communication with the image capture device and the database. The method further includes comparing the captured image with the electronic images in the database and determining if the captured image deviates from those in the database.

The embodiments described herein further include a system having a device for causing a chick to spread its wings, and an image capturing device to capture at least one electronic image of the chick's wings as they are spread. The system further includes a database containing electronic images of male and female wing patterns within the chick's breed, and an image processor in communication with the image capture device and the database. When the captured image of the chick's wings is sent to the image processor, it is compared to the database of chick wing patterns for the breed to determine the gender of the chick.

The device for causing a chick to spread its wings is preferably an angled conveyor or hinged platform. The image capture device may be a digital camera. The image taken of the chick may be a front view image.

The embodiments herein also describe a method for determining the gender of a chick including the steps of providing a moving platform to support a chick, introducing at least one stimuli to cause the chick to spread its wings and capturing at least one image of the chick as it spreads its wings. The method further includes providing a database having a library of digital images therein and providing a computer processor in communication with the image capture device and the database. After the chick spreads its wings, an image is taken of the wings. The image of the chick's wing is compared to the library of digital images to determine the gender of the chick.

DESCRIPTION OF THE DRAWINGS

Other objects, features and advantages of the embodiments will become apparent upon reading the following detailed description and upon reference to the drawings, in which.

The embodiments herein described are not intended to be limiting. It is intended that the embodiments shall cover all alternatives, modifications, and equivalents as defined herein.

DESCRIPTION

Figure 1:
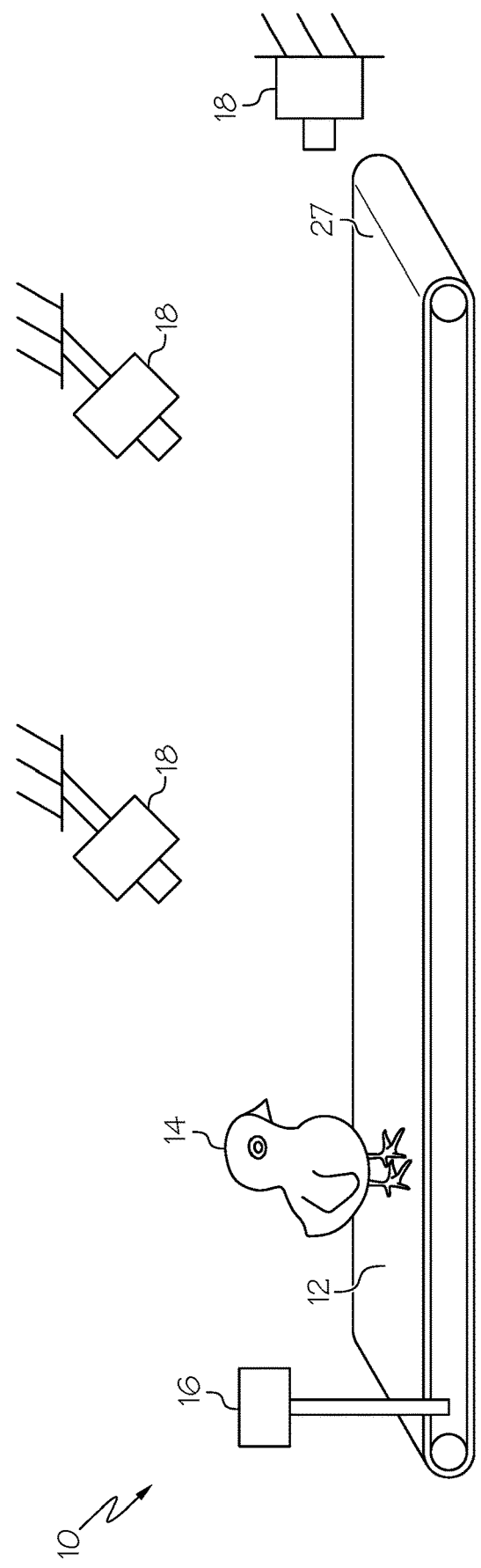
FIG. 1 is a perspective view of a portion of the first embodiment.

The embodiments herein focus on a system and method for determining the relative health and gender of a chick. The first embodiment 10, shown in FIG. 1 includes a first conveyor 12 that moves the chicks 14 in the hatchery. It should be appreciated that the chicks 14 have been previously separated by other conveyors and dividers and are now travelling along the first conveyor 12 in single file fashion. The first conveyor 12 has a presence sensor 16 to sense the presence of a chick 14 on the first conveyor. One or more cameras 18 are located along the pathway of the first conveyor 12. It is preferred that the cameras 18 be located at the end of the conveyor level with the body of the chick 14 so as to be able to focus on the chick's abdomen, legs and feet. In addition, cameras 18 may be mounted overhead the first conveyor 12 to be able to focus on the chick but not interfere with the chick's travel along the first conveyor. The term conveyor is understood to mean any type of handling mechanism capable of transporting an object, in this case an animal, from a first location to a second location. The term conveyor shall include but not be limited to conveyor belts, moving platforms and the like.

Figure 7:
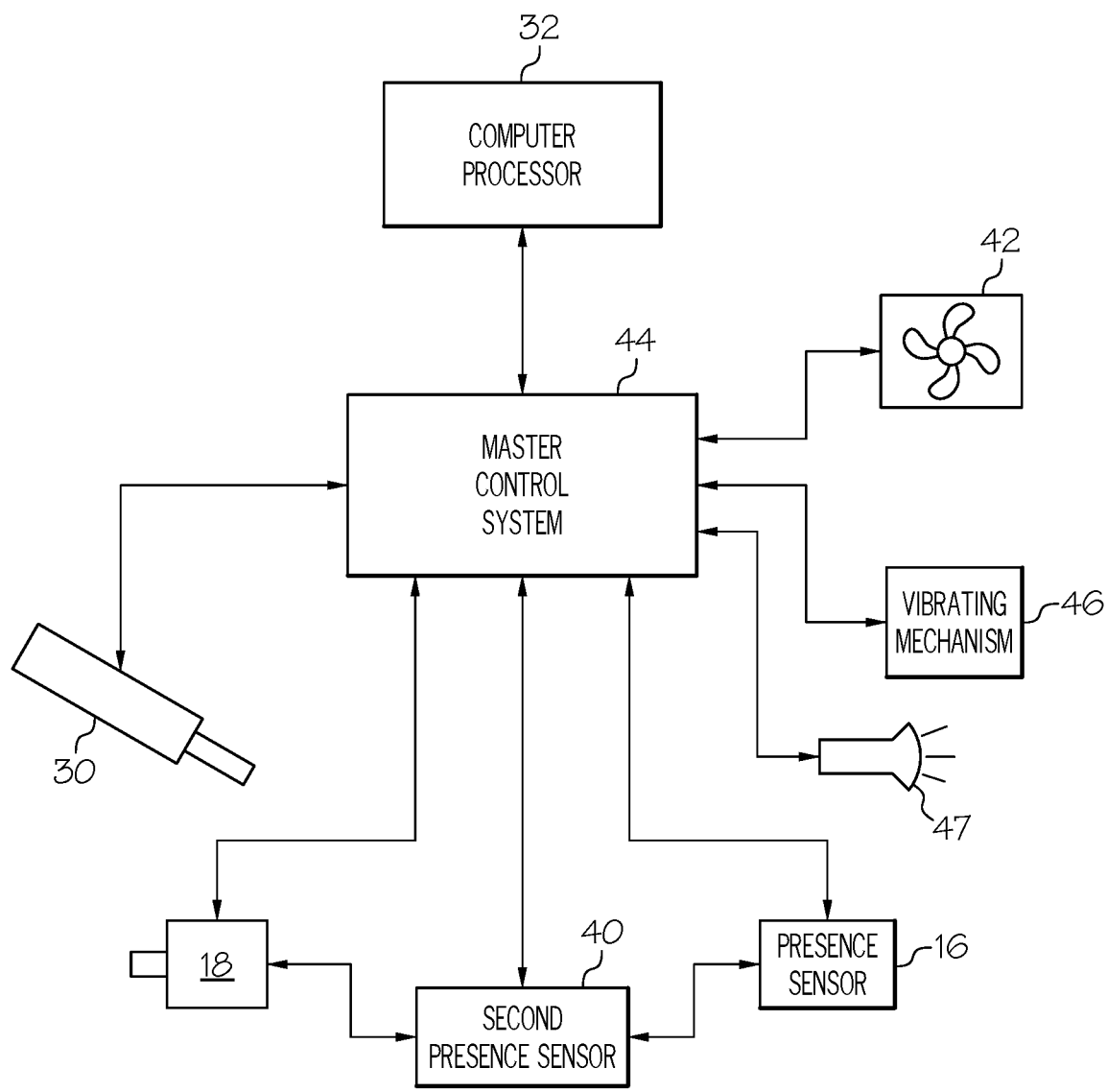
FIG. 7 is a diagrammatic representation of the communication of various elements of the first embodiment.
Figure 8:
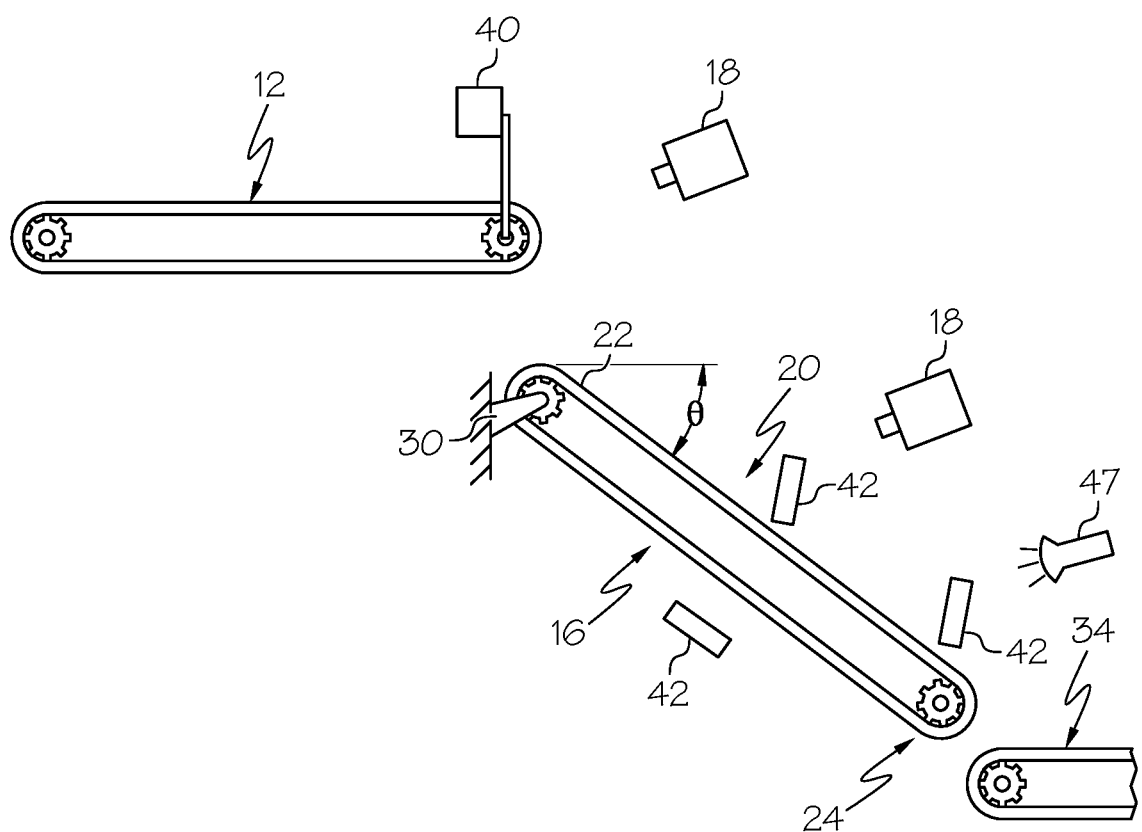
FIG. 8 is a side schematic view of the first embodiment in FIG. 6.

The cameras 18 are preferably video cameras that can take live video footage of each chick 14 as it travels along the first conveyor 12. The cameras 18 are in communication with master system controller 44 and a computer processor 32 (FIG. 7). The computer processor 32 includes a database of images of healthy and unhealthy chicks 14. The computer processor 32 is designed to receive and process the images from the cameras 18 and determine whether or not the chick images show any signs of abnormalities or irregularities that warrant further attention. The details of this process will be discussed below.

Figure 2:
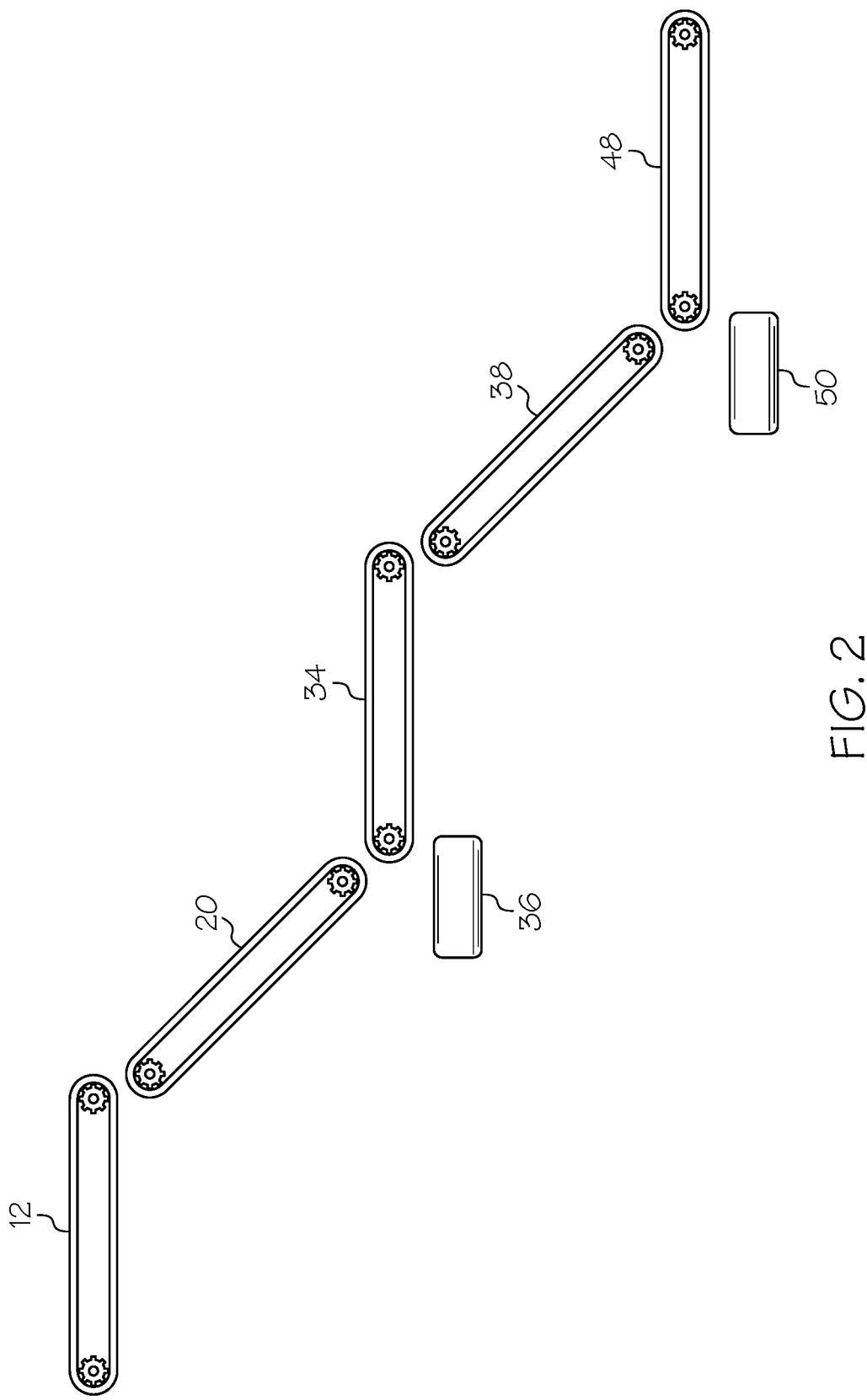
FIG. 2 is a side schematic view of the first embodiment.

As shown in FIG. 2, an angled conveyor 20 is positioned adjacent to and below the first conveyor 12. The first angled conveyor 20 is oriented at an angle θ to the horizon.

Figure 4:
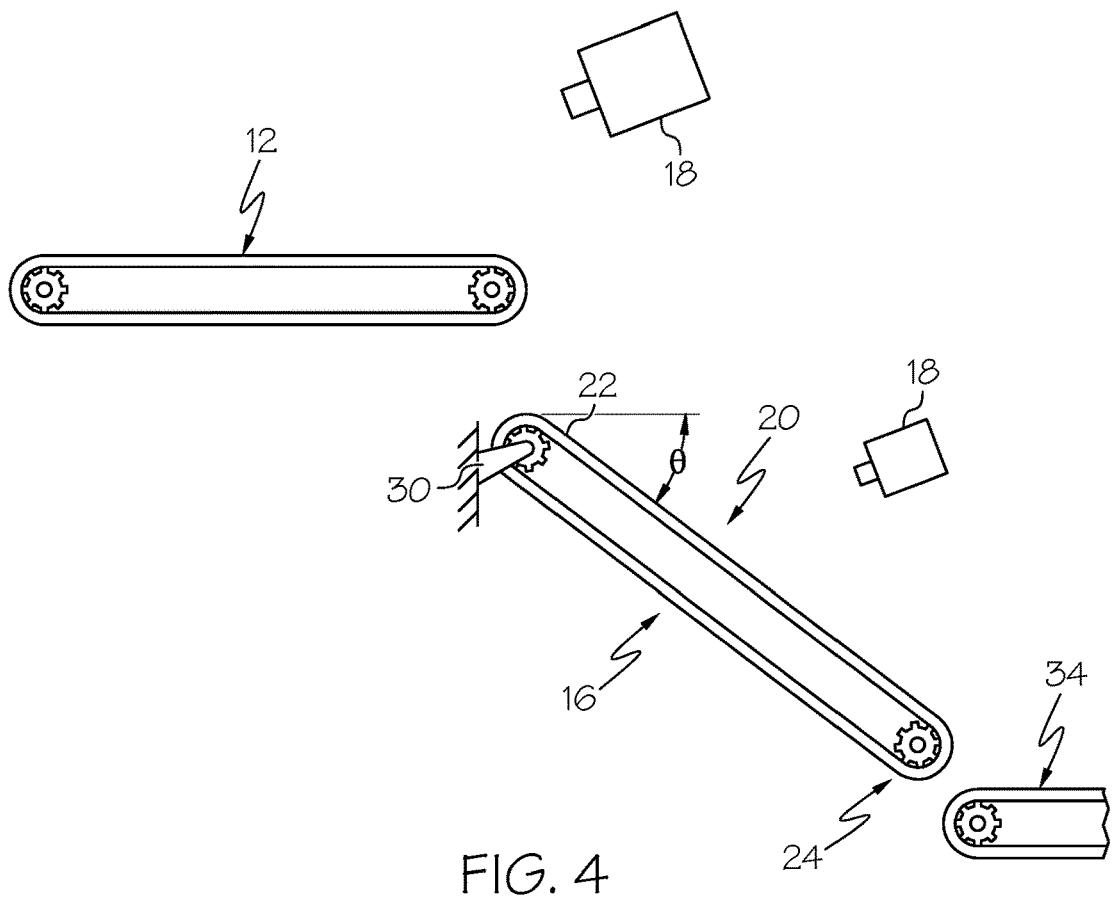
FIG. 4 is an enlarged side schematic view of a portion of the first embodiment of FIG. 2.

The first angled conveyor 20 has a near end 22 and a far end 24. The angled conveyor 20 has a frame 26 to support the angled conveyor (FIG. 4). The frame 26 of the angled conveyor 20 is rotatably connected at the near end 22 to a fixed structure such as the frame structure of the overall system. The frame 26 supports a pair of rails 28 that prevent the chick from falling off of the angled conveyor 20.

Figure 3:
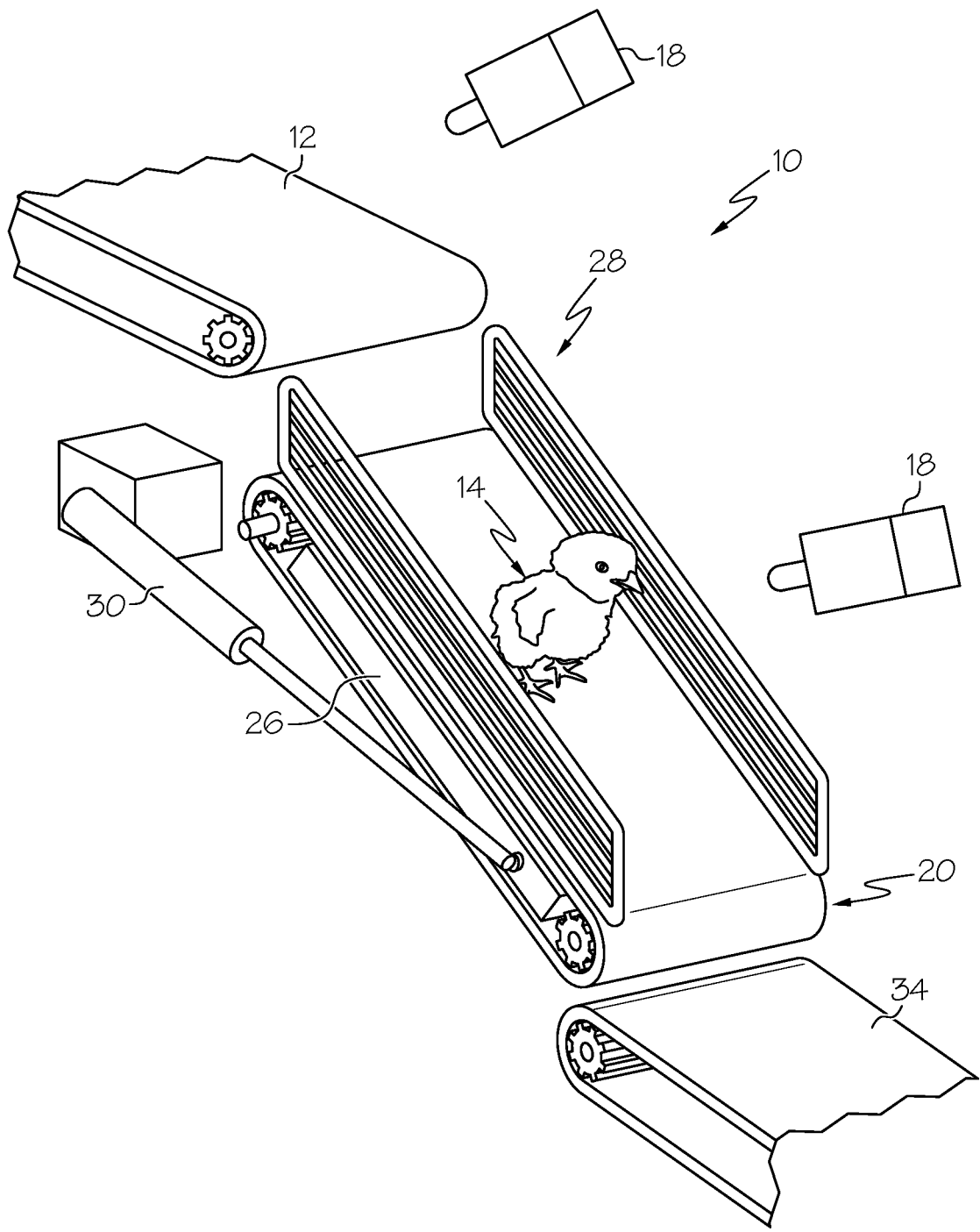
FIG. 3. is an enlarged perspective view of the first angled conveyor of the first embodiment.
Figure 5:
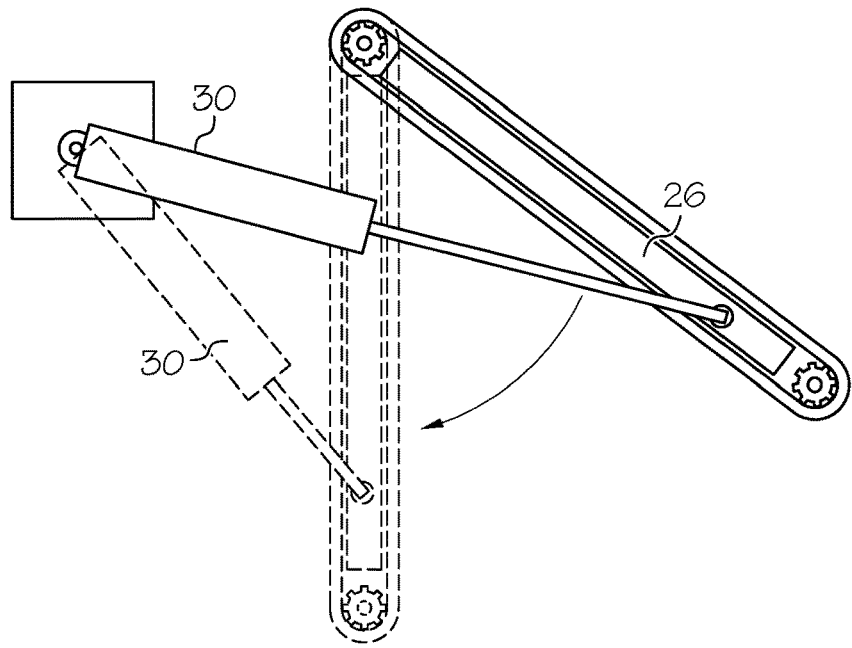
FIG. 5 is diagrammatic representation of the actuator of the first embodiment in both extended and retracted positions.

An actuator 30, shown in FIGS. 3-5, is fixedly connected to the frame 26 of the angled conveyor 20 and also to a support structure such as the frame structure of the overall system. The actuator 30 is positioned normally to support the angled conveyor 20 in an extended position. When activated, the actuator 30 retracts causing the frame 26 of the angled conveyor 20 to pivot about its near end 22 and swing the far end 24 further downward increasing the angle θ. The actuator 30 is in communication with the computer processor 32 that controls the actuator remotely.

Returning to FIG. 2, a third conveyor 34 is located below angled conveyor 20 and is positioned to receive chicks 14 therefrom when the angled conveyor is in its extended position. A fourth conveyor 36 is located further below the angled conveyor 20 and is oriented perpendicularly to the angled conveyor 20, when contracted. The fourth conveyor 36 receives chicks 14 from the angled conveyor 20 when it is retracted by the actuator 30, which will be discussed in more detail below.

Figure 6:
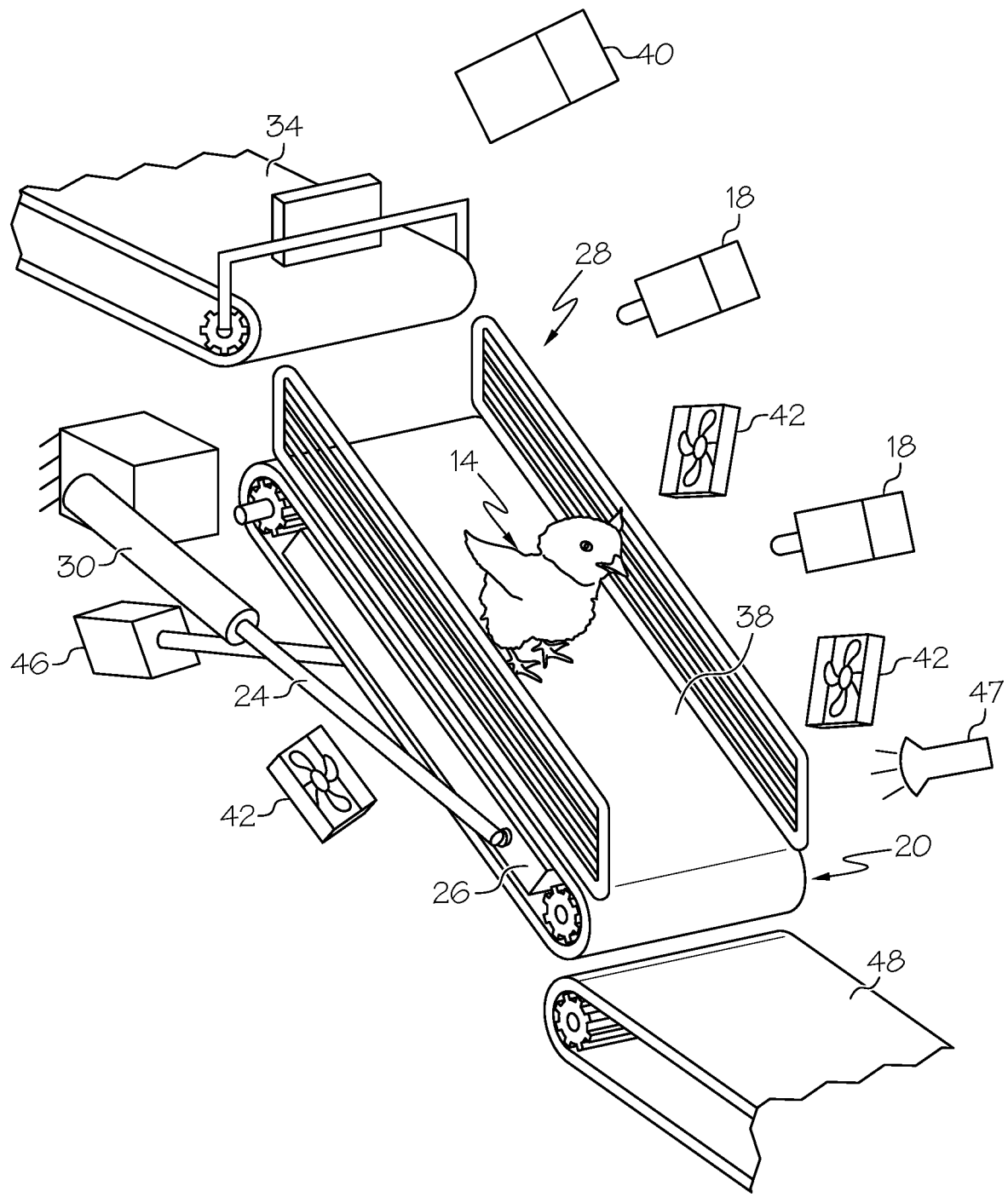
FIG. 6 is an enlarged perspective view of the second angled conveyor of the first embodiment.

A second angled conveyor 38, shown in FIGS. 2 and 6, is located immediately below the third conveyor 34 to receive chicks 14 therefrom. A second presence sensor 40 is located at the end of the third conveyor 34. The second presence sensor 40 senses the presence of a chick 14 along the pathway of the second angled conveyor 38.

Cameras 18 are positioned at the end of the third conveyor 34 and at one or more points along the pathway of the second angled conveyor 38 (FIG. 6). The cameras 18 are positioned to focus on the wing pattern of the chicks 14 as they pass.

Fans 42 are located along the pathway of second angled conveyor 38 (FIG. 6). The fans 42 are positioned so as to direct air upwards as the chick 14 passes. Fan activation is controlled by the master control system 44. The master control system is in communication with the computer processor 32 (FIG. 7).

A vibrating mechanism 46, shown in FIG. 6 is fixed to the second angled conveyor 38. During use, the vibrating mechanism 46 causes the second angled conveyor 38 to vibrate. The vibrating mechanism 46 is in communication with the master control system 44. A strobe light 47 is positioned towards the end and above the pathway of the conveyor 38. The strobe light 47 is also in communication with the master controller 44.

As shown in FIG. 2, a fifth conveyor 48 is located at the end of the second angled conveyor 38. The fifth conveyor 48 receives those chicks 14 coming off of the second angled conveyor 38. A sixth conveyor 50 is positioned directly below and perpendicular to the second angled conveyor 38. The sixth conveyor 50 receives those chicks 14 who are moved off of the second angled conveyor 38 when it is in its retracted position. This process will be explained in more detail below.

The computer processor 32 includes a database having a library of digital images of the wing patterns of chicks of a variety of chicken breed stored therein. The computer processor 32 (FIG. 7) is also in communication with the second presence sensor 40, cameras 18, and actuator 30 (FIG. 6) via the master control system 44. Moreover, the computer processor 32 is also in communication with a master control system 44 which controls the speed of the conveyors and controls the overall function of operation. The master control system 44 is in electronic communication with the cameras 18, fans 42 and vibrating mechanism 46 (FIG. 6) such that the start and stop of each of the aforementioned may be controlled by the master control system. A diagrammatic representation of the communication between the aforementioned elements is shown in FIG. 7.

In use, after the chicks 14 hatch, they are initially processed and eventually moved onto the first conveyor 12. It should be noted that there may be a series of other conveyors—and dividers and the like (not shown) that may be used to move the newly hatched chick 14 to the conveyor 12. However, such equipment and logistics are not discussed herein.

As the chick 14 travels along the first conveyor 12, first presence sensor 16 detects the presence of a chick travelling along the first conveyor 12 (FIG. 2). The presence sensor 16 communicates with the computer processor 32 which activates the cameras 18 positioned at the end of and above the pathway of the first conveyor 12 and along the angled conveyor 20 (FIG. 3). The cameras 18 takes at least one image of the chick. Preferably the camera 18 is able to take video feed of the chick's abdomen, legs, facial features and feet.

The image or images are electronically communicated to the computer processor 32 (FIG. 7). The computer processor 32 processes the images and compares them with those images in its database of healthy and unhealthy chicks of the same breed. In comparing the camera images with the digital image library, the computer processor 32 is able to detect any abnormalities or deviations in the images taken from standard images in the database. If there is a deviation detected in the image taken, the computer processor 32 registers such a deviation as an abnormality or affliction that needs closer attention.

The computer processor thus communicates its finding with the master control system 44 (FIG. 4), which activates the actuator 30. This causes the near end 22 of the first angled conveyor 20 to pivot and the far end 24 to swing downwardly increasing the angle θ. At a certain angle θ, the chick 14 cannot remain on the first angled conveyor and is dropped onto the fourth conveyor 36 (FIG. 2) for further manual inspection. If the chick is unhealthy, it will be separated from the otherwise healthy flock. If the chick is, in fact, healthy, it will be returned to the flock for further processing.

Once the chick has been transferred to the fourth conveyor 36, the actuator 30 (FIG. 5) is reversed and causes the first angled conveyor 20 to return to its extended position. This results in the far end 24 of the first angled conveyor 20 swinging upwardly as the near end 22 pivots about itself and the angle θ declines. Once the actuator has returned the first angled conveyor 20 to its original position, it is ready to receive another chick 14. In this manner, only healthy chicks are permitted to advance to the third conveyor 34.

Once a healthy chick has progressed to the third conveyor 34, the second presence sensor 40 (FIG. 6) detects its presence on the third conveyor 34. The second presence sensor 40 communicates with the computer processor 32 and master control system 44 (FIG. 7) to activate the cameras 18, fans 42, strobe light 47 and vibrating mechanism 46 adjacent to the second angled conveyor 38.

At the end of travel along the third conveyor 34, the chick moves onto the second angled conveyor 38. At this time, the chick encounters the second angled conveyor 38 with air blowing upwardly from its feet towards its face and head created by the fans 42. In addition, the surface of the second angled conveyor 38 is vibrating as a result of the activation of the vibrating mechanism 46. The upwardly blowing air and vibrating surface cause the chick to feel unbalanced. In an effort to regain its balance, the chick begins to lift and flap its wings. As it does the cameras 18 take images of the opened wing pattern. The flashing of the strobe light 47 is also expected to have a similar stimuli effect on the chick.

The images are communicated with the computer processor 32 (FIG. 7) which processes the images and compares them to images of male and female wing patterns within its database for chicks of that breed. In comparing the images, the computer can determine the gender of the chick at issue. If the computer processor 32 determines the chick to be a female, the chick is allowed to proceed to the fifth conveyor 48 where it is crated and transferred to a growing farm. If the chick is determined to be a male, the computer processor 32 activates the actuator 30 which retracts and causes the second angled conveyor 38 to pivot and the far end 20 to swing downwardly increasing the angle θ. At a certain angle θ, the chick 14 cannot remain thereon and is dropped onto an alternate conveyor 50 for further processing. Chicks will be separated by sex and processed separately.

Once the male chick 14 has been transferred to an alternate platform, the master control system 44 deactivates the actuator 30 (FIG. 6). This causes the second angled conveyor 38 to return to its extended position. This results in the far end 20 of the second angled conveyor 38 swinging upwardly as the near end 18 pivots about itself and the angle θ declines. Once the actuator 30 has returned the second angled conveyor 38 to its original position, it is ready to receive another chick.

Thus it is apparent that the embodiments herein provided fully satisfy the objects, aims and advantages set forth above. It is evident that many alternatives, modifications and variations will be apparent to those skilled in the art in light of the foregoing description. Accordingly it is intended to embrace all such alternatives, modifications, and variations as fall within the spirit and scope of the appended claims.

What is claimed is:

1. A system for determining the sex of a chick comprising:
a moving platform to support an unrestrained chick of a particular breed;
at least one stimuli to cause the chick to open its wings;
an image capture device to capture at least one image of the chick; and
a computer processor having a database of images of male and female wing patterns for the particular breed, the computer processor in communication with the image capture device, whereby the image capture device captures at least one image of the chick and transmits it to the computer processor where the image is processed and compared to the database to determine the sex.

2. The system of claim 1 further comprising a master control system in communication with the image capture device, the moving platform, and the computer processor.

3. The system of claim 1 wherein the stimuli may be one or more of the following group: an angled conveyor, a vibrating conveyor, a strobe light, or a stream of air blowing on the chick.

4. The system of claim 1 further comprising a removing device in communication with the computer processor, whereby when the computer processor determines the chick's sex and determines which sex will remain on the moving platform, the removing device is activated and removes a chick having a sex determination different from the determined sex remaining on the moving platform.

5. The system of claim 4 wherein the removing device comprises a moving platform position altering device.

6. A system for determining the health of a day old chick comprising:
   a moving platform upon which an unrestrained chick is supported;
   image capturing device to capture at least one electronic image of the chick;
   computerized image processor in communication with the image capture device, the computerized image processor having access to a database of images of healthy and unhealthy chicks of the same breed, whereby the image capture device captures at least one image of the chick, and it is transmitted to the computerized image processor where the computerized image processor compares the at least one image of the chick to the database of images to detect a deviation from the database of images.

7. The system of claim 6 wherein the image is that of the feet, face, abdomen, wing or legs.

8. The system of claim 6 further comprising a removing device in communication with the computerized image processor, whereby when the deviation is detected, the removing device is activated and removes a chick having the detected deviation from the moving platform.

9. A system of sorting chicks on the basis of a predetermined feature of a chick comprising:
   a moving platform to support an unrestrained chick of a particular breed;
   an image capture device positioned proximate to the moving platform to capture at least one image of the chick as it passes on the moving platform;
   a computer processor in communication with the image capture device, the computer processor having a database of images of a predetermined feature of a chick therein, the computer processor capable of processing images and determining deviation from the database of images; and
   removing means for removing a chick from the moving platform, the removing means in communication with the computer processor, whereby when the image capture device takes an image of the chick and transmits it to the computer processor, the computer processor processes the image and determines any deviation of the image from the database of images, if a deviation is detected, the computer processor communicates with the removing means to remove the chick from the moving platform.

10. The system of claim 9 wherein the predetermined feature is the wing, face, abdomen, or the foot.

11. The system of claim 9 wherein the database of images is limited to those of the chick's breed.

12. The system of claim 9 further comprising a removing device in communication with the computer processor and activated when the computer processor determines the deviation of the image of the chick exceeds a predetermined range, the removing device removes a chick having a variance exceeding the predetermined range from the moving platform.

13. The system of claim 12 wherein the removing device comprises a moving platform position altering device.

14. The system of claim 9 further comprising at least one stimuli proximate to the moving platform.

15. The system of claim 14 wherein the stimuli may be one or more of the following group: an angled conveyor, a vibrating conveyor, a strobe light or a stream of air blowing on the chick.

16. The system of claim 15 wherein the angled conveyor has a near end and a far end and the far end is lower than the near end.

17. The system of claim 16 wherein the angled conveyor is oriented at an angle θ to the horizon.

18. The system of claim 17 wherein the angle θ is between 0 and 90.

* * * * *